United States Patent [19]

Hovey

[11] Patent Number: 4,490,005
[45] Date of Patent: Dec. 25, 1984

[54] ELECTRICAL CONNECTOR

[75] Inventor: Dean L. Hovey, White Bear Lake, Minn.

[73] Assignee: Minnesota Mining and Manufacturing Company, Saint Paul, Minn.

[21] Appl. No.: 390,367

[22] Filed: Jun. 21, 1982

[51] Int. Cl.³ ............................. A61B 5/04; H01R 4/52
[52] U.S. Cl. ................................. 339/278 C; 128/641; 128/803; 339/116 C
[58] Field of Search ............... 128/641, 639, 640, 644, 128/798, 802, 803; 339/75 R, 75 M, 116 R, 116 C, 255 R, 252 R, 278 C, 278 D

[56] References Cited
U.S. PATENT DOCUMENTS

| | | | |
|---|---|---|---|
| 3,610,229 | 10/1971 | Zenkich | 128/641 |
| 3,882,583 | 5/1975 | Gotman et al. | 128/641 |
| 4,271,209 | 6/1981 | De Palma et al. | 427/58 |
| 4,311,152 | 1/1982 | Modes et al. | 128/641 |

*Primary Examiner*—Z. R. Bilinsky
*Attorney, Agent, or Firm*—Donald M. Sell; James A. Smith; William L. Huebsch

[57] ABSTRACT

An electrical connector such as can be used to connect an electrode to its respective lead, which affords relative rotation between the electrode and the lead, while minimizing any abrasion of the conductive surfaces as a result of such rotation in order to maintain the electrical connection between the electrode and the lead. For this purpose either the electrode or lead, or both include a plurality of recessed surfaces coated with a conductive layer which escapes the abrasive rotational interaction and thus remains available to maintain the electrical connection.

1 Claim, 9 Drawing Figures

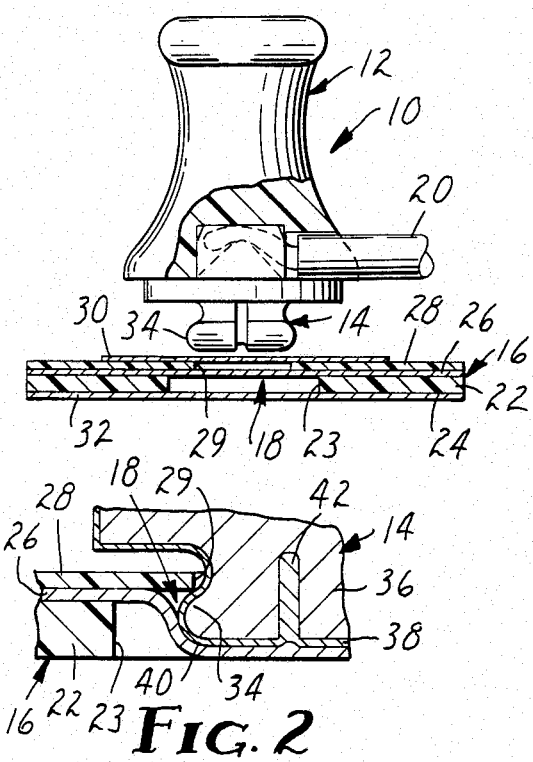
Fig. 1
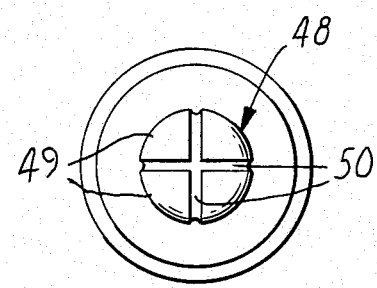
Fig. 3
Fig. 2
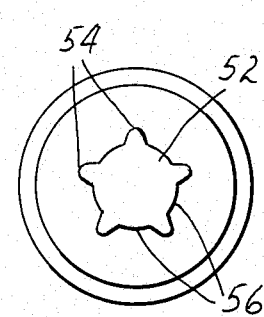
Fig. 4
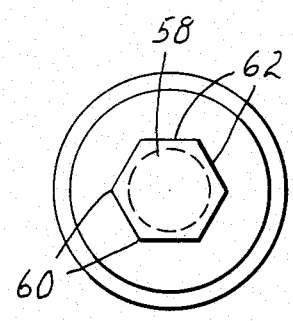
Fig. 5
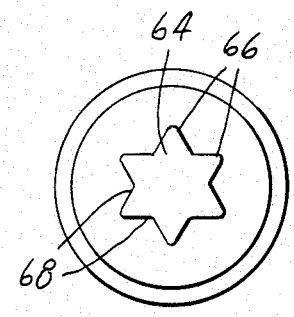
Fig. 6

ELECTRICAL CONNECTOR

The present invention relates to a snap type electrical connector and in particular to an electrical connector which can be utilized to interconnect an electrode to its corresponding lead.

There are numerous configurations for electrical connectors such as those used to interconnect electrodes, for example medical or bio-electrodes, to their corresponding leads. One common connector configuration is a quick disconnect snap type connector wherein one end of the connector terminates in a projecting stud and the corresponding end of the connector terminates in a mating receptacle or socket which receives and secures the stud therein. This type of connector is especially desirable for medical electrodes since it allows the electrodes to be positioned on the subject and then easily connected or disconnected from their corresponding leads. This is even more important with disposable medical electrodes, which are discarded after they are used, and for which a single lead is reused with a number of electrodes. Such a quick disconnect snap type connector within a disposable medical electrode is described in U.S. Pat. No. 3,610,229.

In order to minimize the cost of such disposable electrodes, it is common to form the projecting stud from a nonconductive substrate and then coat that substrate with a very thin coating of a conductive material. This thin coating of conductive material is easily abraded away when the outer wall portions of the stud contact and slide against the wall portions forming the interior of the receptacle, e.g., when such an electrode rotates with respect to its lead wire. The resulting abrasion of the conductive coating as a result of the frictional contact between the mating surfaces of the stud and the receptacle can eventually degrade the electrical conductivity between the electrode and the lead. To minimize this degradation, structures can be provided within the connector to prevent any relative rotation between the electrode and the lead. For example, the electrode described in the '229 patent includes "a plurality of alternating minute grooves and ridges to insure complete electrical conductivity between the male and female parts of the snap fastener and to prevent relative rotation therebetween" (Column 1, lines 45 through 47). This structure, in preventing the relative rotation between the electrode and the lead, also restricts the versatility and ease of manipulation for the electrode, as well as the equipment to which the electrode is connected and the lead running therebetween.

SUMMARY OF THE PRESENT INVENTION

Contrastingly, the present invention relates to a quick disconnect snap type electrical connector such as can be utilized to easily interconnect an electrode with its respective lead, which affords relative rotation between the electrode and the lead, while minimizing the detrimental effects caused by any abrasion of the conductive surface as a result of movement between the electrode and the lead.

This connector comprises a first part including a projecting stud and a second part including a receptacle having wall portions which are adapted to rotatably receive and secure the stud within the receptacle. The projecting stud is formed from a nonconductive substrate having a conductive layer coated thereon. However, the nonconductive substrate of the present invention includes first wall segments disposed to engage the wall portions of the receptacle to position and secure the stud therein, and second wall segments which are recessed from the first wall segments so as to be spaced from the wall portions of the receptacle, when the stud is within the receptacle. This spacing between the second wall segments and the receptacle wall portions allows the second wall segments to escape abrasive contact with the wall portions of the receptacle as the stud rotates with respect to the receptacle. Hence, although the conductive coating on the first wall segments may be progressively abraded away by the relative rotation, the conductive coating on the second wall segments, which are initially spaced from the wall portions of the receptacle, is not abraded away and remains available to maintain electrical contact with the wall portions of the receptacle.

BRIEF DESCRIPTION OF THE DRAWINGS

The present invention will be further described hereinafter with reference to the accompanying drawing wherein:

FIG. 1 is an enlarged frontal view of a connector according to the present invention, with portions broken away to reveal internal structure therein;

FIG. 2 is a partial and enlarged vertical sectional view of the projecting stud after it has been inserted into the electrode shown in FIG. 1;

FIGS. 3 through 7 are alternate embodiments of the projecting stud illustrated in FIG. 1.

DETAILED DESCRIPTION

Figure 7:
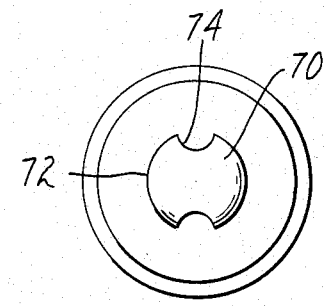

The connector 10 of the present invention, as illustrated in FIG. 1, comprises a first part 12 including a projecting stud 14, and a second part 16 including a receptacle having wall portions 18 adapted to rotatably receive and secure the stud 14 within the receptacle. In the illustrated connector 10, this first part 12 forms the lead end of the connector. Hence, the first part 12 also includes a lead wire 20 which is secured in electrical contact with the projecting stud 14. The second part 16 of the connector, accordingly, forms the electrode end. In this embodiment the electrode includes a flexible substrate 22, having a central interior opening 23 die-cut therethrough. One surface 24 of the substrate 22 is coated with an adhesive to adhere the electrode to a subject to be monitored or treated, and the opposing surface supports a pad 26 extending over the opening 23, which pad 26 is saturated with a conductive gel. This pad 26 and the gel therein are protected with a resilient cover sheet 28. When the pad 26 is depressed into the opening 23 such that it becomes spaced from the cover sheet 28, this combination forms the wall portions 18 defining the receptacle adapted to receive the stud 14. As manufactured, the electrode further includes an adhesive coated tab 30 which adheres to the cover sheet 28 and closes an opening 29 within the cover sheet 28 which leads into the receptacle, and a release liner 32 which adheres to the adhesive coated surface of the substrate 22 and closes the opposing end of the opening 23 to prevent desiccation of the gel as well as to prevent the degradation of the adhesive on the substrate 22.

FIG. 2 illustrates the electrode joined or connected with the lead by the connector 10 of the present invention. As can be seen, the tab 30 has been pulled away to permit the stud 14 to enter the receptacle. A lip 34 on the stud 14 which is slightly larger in circumference than the opening 29, interacts with the resilient cover sheet 28 to secure the stud within the receptacle. The electrode as illustrated also has the liner 32 removed, since the electrode is usually attached to the subject prior to connecting the lead.

As has already been described, the electrode is typically adhesively affixed to the subject being monitored or treated. The adhesive-skin interface of the electrode, however, imposes a limitation on the amount of movement the subject can make or in any desired relocationing or repositioning of the equipment to which the electrodes are connected. This is because excessive movement of the subject, equipment or the leads can potentially dislodge the electrode from the subject. To minimize this potential, it is desirable that provision be made within the electrode assembly for affording at least rotational movement between the electrode and the lead, in order to relieve some of the stress which might be applied to the adhesive-skin interface. This relative rotation capability would allow at least limited movement by the subject, and/or of the equipment, and provide some manipulative versatility for the placement of the electrode and/or of the equipment and leads during the monitoring procedure, without severely disrupting the measurements being made. The quick disconnect snap type connector is ordinarily capable of affording this rotational movement, however, as previously explained the disposable electrode's ability to rotate with respect to the lead can cause a degradation of the electrical contact between the lead and the electrode as the frictional contact between the lead and the electrode abrades away the conductive coating on the stud 14.

This is even more of a problem with disposable electrodes, where in an effort to reduce manufacturing costs, the projecting stud 14 is molded from a non-conductive polymeric material 36, and then coated with a thin conductive material 38 such as silver, to establish the electrical contact with the electrode. As the projecting stud of the lead is inserted within the electrode, the pad 26 and the conductive gel therein conform to the profile of the stud 14 thereby establishing the electrical contact between the lead and the electrode. This construction affords the rotation of the stud 14 within the receptacle. It does not however, prevent the introduction of frictional contact between the stud 14 and the pad 26 with the conductive gel therein, resulting from this rotation. The present invention recognizes this, and includes structure to maintain the integrity of the electrical connection between the electrode and the lead in spite of this frictional contact, without restricting the ability to rotate the electrode with respect to the lead. This is done by including within the stud 14, first wall segments 40 which are disposed to engage the wall portions 18 of the receptacle and to position and secure the stud 14 therein, and second wall segments 42 which are recessed from the first wall segments 40 so as to be spaced from the wall portions 18 of the receptacle when the stud is inserted therein. This spacing allows the second wall segments 42 to escape the abrasive contact with the wall portions 18 of the receptacle. Hence, although the conductive coating 38 on the first wall segments 40 is potentially abraded away by the relative rotation between the lead and the electrode, there remains sufficient conductive coating 38 on the second wall portions 42 which is not initially removed, due to the spacing, and which therefore remains available to maintain the electrical contact with the wall portions 18 forming the receptacle. The connector 10 of the present invention can thus undergo considerable rotation between the lead and the electrode portions without suffering from the electrical degradation typically present within the existing disposable snap type connectors.

FIGS. 3 through 7 show a variety of configurations for the stud portion of the connector. These configurations have in common the presence of first and second wall segments, with the first wall segments securing and locating the stud within the corresponding receptacle and the second wall segments being spaced from the wall portions of the receptacle to ensure continued electrical integrity. In FIG. 3 the stud 48 has been divided into a plurality of separate sectors with wall segments (i.e., second wall segments 50) between and separating the various sectors, in order to provide the continued electrical contact. As usual, the outwardly exposed periphery of the sectors (first wall segments 49) is used to secure the stud 48 within the receptacle (not shown) and establish the initial electrical contact. FIG. 4 utilizes a stud 52 wherein the first wall segments 54 form a plurality of outward projections from a smaller circumferenced periphery formed by the second wall segments 56. (The second wall segments 56 are therefore recessed from the outwardly projecting first wall segments 54.) FIG. 5 shows a projecting stud 58 having a plurality of facets formed by the second wall segments 62, wherein the outwardly projecting intersections between the facets are formed by the first wall segments 60. FIG. 6 illustrates a projecting stud 64 which is very similar to that illustrated in FIG. 4. Again, this projecting stud 64 has a plurality of outward projections formed by the first wall segments 66 and a plurality of recesses between these projections formed by the second wall segments 68. FIG. 7 illustrates a projecting stud 70 having a plurality of undercut areas formed by the second wall segments 74 with a general outer periphery formed by the first wall segments 72. All of these various embodiments, although looking considerably different, will still function to retain the integrity within the electrical connection between the stud and the receptacle portions of the connector, in spite of repeated rotational abrasion.

Figure 8:
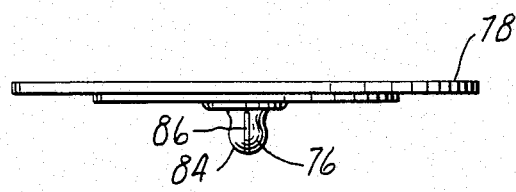
FIGS. 8 and 9 are elevational views of the two portions of an alternate embodiment of a connector according to the present invention, FIG. 9 having parts thereof broken away and shown in section.
Figure 9:
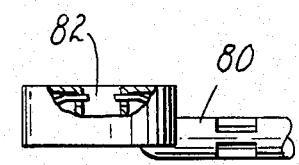

FIGS. 8 and 9 show an embodiment of the present invention wherein the projecting stud portion 76 of the connector is part of the electrode 78 (FIG. 8) as opposed to the lead 80 (FIG. 9). The lead 80 therefore includes the receptacle 82. The stud 76 still includes first wall segments 84 and second wall segments 86 having the relationship described above.

Having thus described several embodiments of the present invention, it will be understood that changes may be made in the size, shape, or configuration of some of the elements described herein without departing from the present invention as recited in the appended claims.

I claim:

1. In a stud of the type having a central axis and comprising a non conductive substrate and a thin electrically conductive outer layer over said substrate, said substrate and conductive outer layer providing a base portion adapted to be connected to a part of a first connector portion, an axially spaced distal end portion adapted to be received in a socket defined in a second connector portion with the conductive outer layer on said distal portion in engagement with a conductive wall defining said socket, and a central portion between said base and distal end portions adapted to be frictionally engaged by means in said second connector portion for releasably retaining said distal portion of said stud in said socket while affording relative rotation about said axis between said second connector portion and said stud, the improvement wherein said central portion of the stud includes first outer wall segments adapted to be engaged by said means for releasably retaining and second wall segments recessed from said outer wall segments and the means for releasably retaining, said second wall segments extending from said distal end portion to said base portion to retain electrical continuity therebetween despite abrasion of said conductive outer layer from said outer wall segments in said central portion by said means for releasably retaining.

* * * * *